United States Patent [19]

Lerner

[11] Patent Number: 5,357,968
[45] Date of Patent: * Oct. 25, 1994

[54] DIAGNOSING AND TREATING SUBACUTE MYOCARDITIS

[76] Inventor: Albert M. Lerner, 660 Woodland, Birmingham, Mich. 48009

[*] Notice: The portion of the term of this patent subsequent to May 25, 2010 has been disclaimed.

[21] Appl. No.: 938,439

[22] Filed: Aug. 31, 1992

Related U.S. Application Data

[63] Continuation-in-part of Ser. No. 675,542, Mar. 25, 1991, Pat. No. 5,213,106.

[51] Int. Cl.$^5$ .......................................... A61B 5/0452
[52] U.S. Cl. .................................. 128/696; 128/702; 128/704; 128/706
[58] Field of Search ............... 128/704, 706, 696, 702, 128/707

[56] References Cited

U.S. PATENT DOCUMENTS

| | | |
|---|---|---|
| 3,267,934 | 8/1966 | Thornton . |
| 3,572,321 | 3/1971 | Bloomfield et al. . |
| 3,595,218 | 7/1971 | Kirkpatrick et al. ............... 128/707 |
| 3,605,727 | 9/1971 | Zenevich et al. . |
| 3,829,766 | 8/1974 | Herz . |
| 3,858,034 | 12/1974 | Anderson . |
| 3,868,567 | 2/1975 | Ekstrom . |
| 4,183,354 | 1/1980 | Sibley et al. . |
| 4,275,742 | 6/1981 | Faisandier . |
| 4,457,315 | 7/1984 | Bennish . |
| 4,546,776 | 10/1985 | Bellin et al. . |
| 4,583,553 | 4/1986 | Shah et al. . |
| 4,622,980 | 11/1986 | Kunig . |
| 4,784,153 | 11/1988 | Marks . |
| 4,854,327 | 8/1989 | Kunig . |
| 4,883,065 | 11/1989 | Kelen . |
| 4,987,901 | 1/1991 | Kunig . |
| 5,197,480 | 3/1993 | Gebhardt ............................ 128/702 |

OTHER PUBLICATIONS

Chest Magazine, Nov. 1988 article by Terrence J. Montague and commentary.

Primary Examiner—William E. Kamm
Assistant Examiner—Kennedy J. Schaetzle
Attorney, Agent, or Firm—Brooks & Kushman

[57] ABSTRACT

A method for diagnosing subacute myocarditis is performed by electrocardiographically monitoring an ambulatory patient who has unexplainable fatigue and determining the frequency when the T-wave of the ambulatory patient is not positive. This monitoring is preferably performed by a portable monitor and the data is magnetically stored so as to permit subsequent analysis. A treatment is prescribed, preferably restricting activity and refraining from the intake of alcohol as well as antiviral chemotherapy and immunomodulators, when there is an excessively high frequency of the T-wave not being positive. Recovery is determined by further electrocardiographic monitoring of the ambulatory patient and noting when the normally positive T-waves are present all, or at least almost all, of the time.

20 Claims, 1 Drawing Sheet

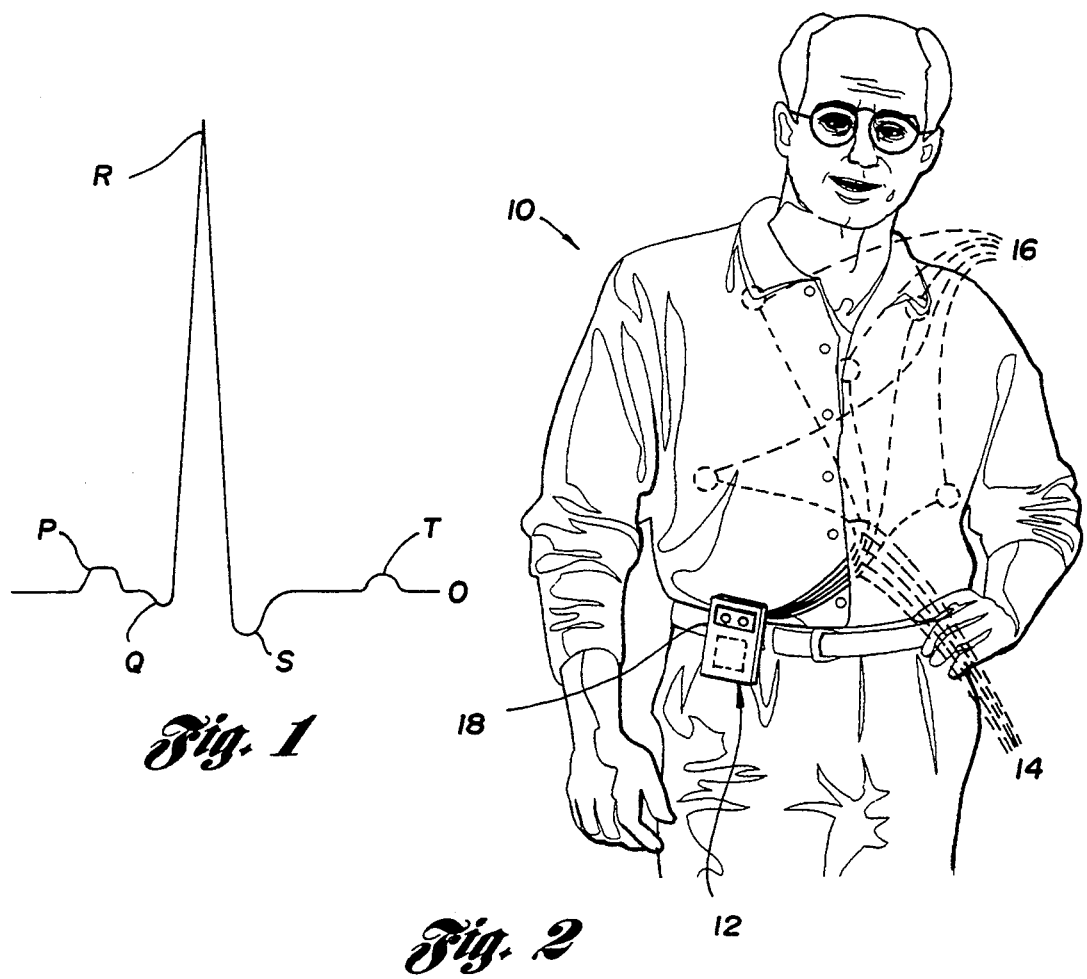
Fig. 1
Fig. 2
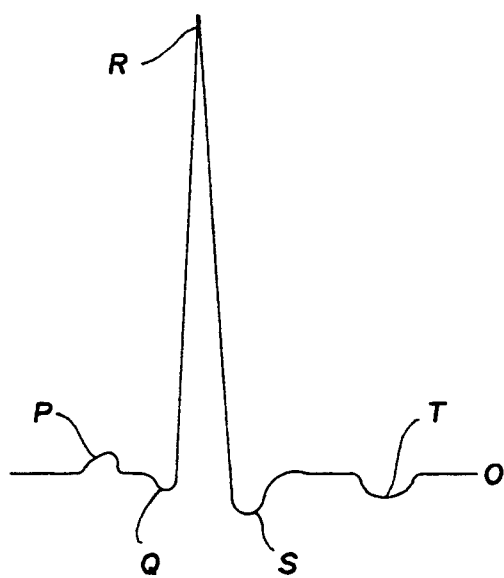
Fig. 3
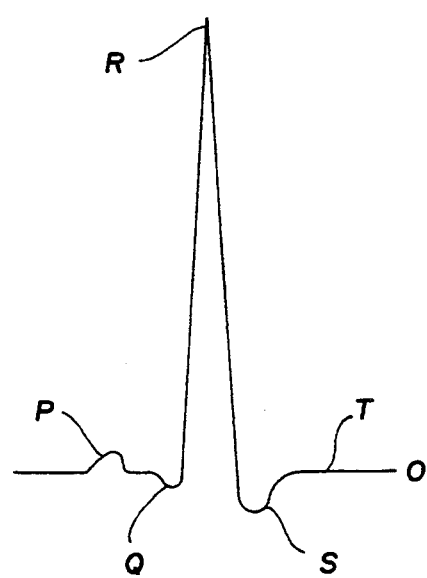
Fig. 4

DIAGNOSING AND TREATING SUBACUTE MYOCARDITIS

CROSS REFERENCE TO RELATED APPLICATION

This application is a continuation-in-part of pending prior application Ser. No. 675,542 filed on Mar. 25, 1991 by Albert M. Lerner under the title "Diagnosing and Treating Chronic Fatigue Syndrome By Electrocardiographic Monitoring Of T-Waves" now U.S. Pat. No. 5,213,106.

TECHNICAL FIELD

This invention relates to a method for diagnosing and treating subacute myocarditis, i.e. cardiac dysfunction by electrocardiographic monitoring.

BACKGROUND ART

The medical community now recognizes a condition of unknown cause that is referred to as chronic fatigue syndrome. The role of cardiac dysfunction in this syndrome, the diagnosis and preferred treatment have not been heretofore understood or explainable. A competent diagnosis for fatigue will conventionally include a complete medical history, a physical examination and appropriate laboratory studies in order to determine whether the fatigue can be explained by other diagnoses such as arteriosclerosis or other coronary artery disease, heart muscle damage from coronary thrombosis or other acute heart disease, or other heart damage such as myocarditis or pericarditis, etc. Other recognizable infections or other diverse maladies may, of course, cause chronic fatigue; but, as mentioned above, this syndrome has not been heretofore understood or diagnosable. Also, while some consider chronic fatigue syndrome to exist only when it persists for six months or longer, others consider this syndrome to be present when there is an unexplainable fatigue for much shorter periods of time such as one or two months.

Conventional diagnosis for heart disease includes electrocardiographic monitoring which has been done for many years such as disclosed, for example, by U.S. Pat. Nos.: 3,267,934 Thornton; 3,572,321 Bloomfield et al; 3,829,766 Herz; and 4,275,742 Faisandier. Most electrocardiographic monitorings are performed on a sedentary patient; however, it is also conventional to electrocardiographically monitor an ambulatory patient such as disclosed by U.S. Pat. Nos.: 4,183,354 Sibly et al; 4,457,315 Bennish; 4,546,776 Bellin et al; 4,583,553 Shah et al; and 4,883,065 Kelen.

Conventional analysis of electrocardiograms of both sedentary and ambulatory patients has recognized that heart disease can be diagnosed from a persistent abnormality in the PQRST waveform generated by the electrocardiographic monitoring. For example, when the PQRST waveform for a patient almost always has depressed ST segments or depressed T-waves, it is recognized that this is an indicator of a lack of myocardial oxygen that can result from arteriosclerosis, heart damage such as from coronary thrombosis, myocarditis or pericarditis. Prior art which discloses analysis of electrocardiographic data includes U.S. Pat. Nos.: 3,605,727 Zenevich et al; 3,858,034 Anderson; 3,868,567 Ekstrom; 4,622,980 Kunig; 4,784,153 Marks; 4,854,327 Kunig; and 4,987,901 Kunig as well as Chest Magazine, November 1988 article by Terrence J. Montague and the commentary on this article by the inventor of the present application in analyzing T-wave depression and inversions.

DISCLOSURE OF INVENTION

An object of the present invention is to provide a method for diagnosing and treating subacute myocarditis of a patient who has unexplainable fatigue.

In carrying out the above object, the method is performed on the patient with unexplainable fatigue while the patent is ambulatory such as during a 24 hour period during which the frequency is determined when the T-wave is not positive, i.e. horizontal or inverted so as to be negative. A diagnosis of subacute myocarditis is then made based on the determination of T-wave frequency. More specifically, it has been discovered that horizontal or negative T-waves of even a relatively small frequency of the total for any given time period can be an indication of subacute myocarditis which may occur during the course of one or several systemic infections following an earlier vital infection.

In carrying out the method, it is preferably to utilize a portable monitor to perform the electrocardiographic monitoring of the ambulatory patient such that the monitoring can be performed for a prolonged time period during normal daily activity. Most preferably, the data from the electrocardiographic monitoring is magnetically stored so as to facilitate its analysis to detect the frequency when the T-wave is not positive.

In analyzing the electrocardiographic data, the number of cycles when the T-wave is not positive during a given time period is utilized as the numerator of a ratio whose denominator is the total number of cycles during the given time period such that multiplication of this ratio by 100 gives the percentage of cycles when the T-wave is not positive.

Monitoring of the frequency when the T-wave is not positive can be performed at different time periods to diagnose the presence and severity of the patient's subacute myocarditis. More specifically, the frequency when the T-wave is not positive can be determined for a time period when the patient's pulse rate is below 100 cycles per minute such as during normal activity. Furthermore, the frequency when the T-wave is not positive can be determined for a time period when the patient's pulse rate is between 100 and 120 cycles per minute such as during modest tachycardia. Still further, the frequency when the T-wave is not positive can be determined for a time period when the patient's pulse rate is above 120 cycles per minute such as during severe tachycardia. In addition, the frequency when the T-wave is not positive can be determined for a given time period regardless of the patient's pulse rate. A higher frequency of the T-wave not being positive for any given pulse rate or the same frequency of the T-wave not being positive at a lower pulse rate is believed to be indicative of more severe subacute myocarditis.

The treatment prescribed can be restricting activity, refraining from the intake of alcohol, antiviral chemotherapy or immunomodulators. The recovery is also preferably monitored by performing further electrocardiographic monitoring of the treated ambulatory patient and determining the frequency when the T-wave is not positive.

The objects features and advantages of the present invention are readily apparent from the following detailed description of the best mode for carrying out the invention when taken in connection with the accompanying drawings.

BRIEF DESCRIPTION OF DRAWINGS

FIG. 1 is a view of an electrocardiogram of a healthy person;

FIG. 2 is a partial view of an ambulatory patient being monitored for subacute myocarditis in accordance with the present invention; and FIGS. 3 and 4 are electrocardiograms illustrating inverted and horizontal T-waves, respectively, which are utilized to determine the frequency when the T-wave of the monitored ambulatory patient is not positive in order to diagnose subacute myocarditis in accordance with the present invention.

BEST MODE FOR CARRYING OUT THE INVENTION

With reference to FIG. 1 of the drawings, an electrocardiogram of a healthy person is illustrated and an understanding thereof will be helpful in understanding the electrocardiographic monitoring of the present invention. This electrocardiogram includes a PQRST waveform corresponding to one heart beat cycle. The P-wave is of a positive polarity and corresponds to an electrical impulse that triggers the heart beat. After the P-wave, there is a quiescent PQ segment that lasts for approximately 0.04 seconds prior to the QRS segment which corresponds to ventricular contractions producing the actual pumping of the heart and including a slightly negative initial Q-wave, the large positive R-wave and the slightly negative S-wave. Following the ST segment, there is a T-wave which corresponds to repolarization of the heart in preparation for the next cycle. It should be noted that it is already recognized that a persistently negative ST segment which has a negative value throughout as well as persistently depressed or inverted T-waves are already recognized as demonstrating heart scar or ischemia that would thus explain fatigue according to conventional diagnosis.

The electrocardiographic monitoring findings discussed below were observed during a study of a group of 25 individuals and concentrated on ten, with a mean age of 37 years, who had fatigue that was not explainable by conventional analysis. All but one of these individuals were relatively young, i.e. under 50 years of age, and were predominantly individuals who previously were relatively active as opposed to lethargic. They did not have hypertensive vascular disease, coronary artery disease, diabetes mellitus or hyperlipidemia which are increased risk factors for coronary artery occlusion.

With reference to FIG. 2, a method for diagnosing subacute myocarditis is performed in accordance with the present invention by electrocardiographically monitoring an ambulatory patient 10 who has unexplainable fatigue, i.e. the patient does not have an electrocardiogram whose ST segment is persistently depressed or whose T-waves are persistently inverted. This electrocardiographic monitoring is performed with a monitor 12 as is hereinafter more fully described. In carrying out the method, the frequency is determined when the T-wave of the ambulatory patient is not positive. In other words, this patient may demonstrate a normal electrocardiogram like that shown in FIG. 1 during most of the cycles; however, during a limited number of cycles such as on the order of 0.1% or so to 20 or 25% of the total, the T-wave may be either inverted as shown in FIG. 3 or horizontal as shown in FIG. 4 so as thus not to be positive. A determination of this frequency of the T-wave not being positive in an ambulatory patient whose fatigue has not been heretofore explainable demonstrates subacute myocarditis which may result from a viral infection or other unrecognized infectious agent that precedes the onset of the fatigue usually by a time period of several days or a week or more.

With continuing reference to FIG. 2, the monitor 12 utilized to perform the electrocardiographic monitoring of the ambulatory patient is preferably of the portable type so that the patient does not have to stay at the medical facility where the monitoring is commenced and can thus be monitored during normal daily activity. Monitor 12 has five leads 14 with connections 16 to the patient's body so that the electrical charge between different locations can be determined in any conventional way to provide the electrocardiographic monitoring. The data from the electrocardiographic monitoring is preferably magnetically stored such as on a magnetic tape cassette 18 inserted into the monitor in a conventional manner. It should be recognized that the data can also be sent from the monitor by telemetry for magnetic storage at a suitable pickup station; however, the magnetic storage by a tape cassette held by the portable monitor is preferred.

The monitoring was performed both (1) between the two upper leads (normally referred to as "standard lead one") to give an overall monitoring of the heart, and (2) between the leads connected to the left shoulder and the center of the chest to monitor the left ventricle which provides pumping of blood from the heart. However, it should be stated that it is believed that the same results will be observed between other leads as the results herein discussed. Furthermore, the presence of the T-waves that are not positive (1) at one particular lead such as the lead that monitors the left ventricle, and/or (2) at more than one lead is believed to indicate more severe subacute myocarditis.

The patient is monitored as described above for a given time period such as normally 6 hours, 12 hours, 18 hours or more conventionally 24 hours, although a greater time can also be monitored, and the number of cycles when the T-wave is not positive is counted in any conventional way. The number of cycles when the T-wave is not positive during a given time period may be utilized as the numerator of a ratio whose denominator is the total number of cycles during the given time period. Thus, multiplication of that ratio by 100 gives the percentage of cycles when the T-wave is not positive. Any healthy person may have a limited number of cycles with the T-wave not being positive during the 80,000 to 140,000 or so daily heart beats at a normal pulse rate. However, a person who has an excessively high frequency of T-waves that are not positive, about 0.1% or greater, may have cardiac dysfunction such as subacute myocarditis that accounts for the fatigue which is otherwise unexplainable.

Different ways of monitoring the fatigue can be useful in diagnosing the patient's heart dysfunction. More specifically, the frequency when the T-wave is not positive may be determined for a time period when the patient's pulse rate is below 100 cycles per minute such as during normal activity. Furthermore, the frequency may be determined when the T-wave is not positive for a time period when the patient's pulse rate is between 100 and 120 cycles per minute such as during modest tachycardia. Still further, the frequency when the T-wave is not positive may be determined for a time period when the patient's pulse rate is above 120 such as during severe tachycardia. Finally, the frequency when the T-wave is not positive may be determined for a given time period regardless of the patient's pulse rate. All of this determination can be performed with any conventional type of electrocardiographic monitoring equipment or conventional equipment suitably adapted so that the attending physician does not have to individually analyze inked tracings of the PQRST waveforms.

The present invention also contemplates treatment of subacute myocarditis upon diagnosing a patient by the method described above. More specifically, when an ambulatory patient having unexplainable fatigue is electrocardiographically monitored and determined to have an excessively high frequency of T-waves that are not positive, a suitable treatment is prescribed. Preferred treatments to be prescribed include restricting activity and refraining from the intake of alcohol, with both being preferred. Other treatments include antiviral chemotherapy and immunomodulators such as cytokines or interferons. Various combinations of these treatments can also be used.

It is also preferable to monitor the treated patient to determine when recovery has been achieved. This further monitoring of the treated patient is performed by conducting further electrocardiographic monitoring of the ambulatory patient, preferably with the portable monitor 12, and determining the frequency of when the T-wave is not positive. Recovery is heralded by reestablishment of the normally positive T-waves; in the patients treated as described above, this recovery took place in a mean time of about eight months. The restricted activity and refraining from the intake of alcohol before recovery is believed to prevent permanent heart damage that would result if this treatment were not followed.

It should also be noted that the extent to which the T-waves are negative is indicative of more severe subacute myocarditis. More specifically, the integral sum of the negative area of the T-waves can be totaled for a given time and divided by the total heart beats during that time, and the result can be expressed as an index or ratio that provides an indication of how severe a case is present. Furthermore, the extent of the negative T-wave can also be measured with a greater negative value, i.e. amplitude, indicating a more severe case of subacute myocarditis. In other words, horizontal T-waves are a less severe case than deeply negative T-waves. Recovery is thus indicated by this indicator becoming smaller as the T-waves are less negative.

Furthermore, it should be understood that T-waves normally become depressed or inverted when a patient stands up in about 4% of patients. As such, the monitoring must account for this consideration.

While the best mode for carrying out the invention has been described in detail, those familiar with the art to which this invention relates will recognize various alternative ways of performing the invention as defined by the following claims.

What is claimed is:

1. A method for diagnosing subacute myocarditis in a patient whose sedentary electrocardiogram ST segment and T-wave do not indicate myocarditis, the method comprising:
   electrocardiographically monitoring to detect T-waves of an ambulatory patient who has unexplainable fatigue;
   determining the T-wave frequency when the T-wave of the ambulatory patient is not positive; and
   providing a diagnosis of subacute myocarditis based on the determination of T-wave frequency.

2. A method for diagnosing subacute myocarditis as in claim 1 wherein a portable monitor is utilized to perform the electrocardiographic monitoring of the ambulatory patient.

3. A method for diagnosing subacute myocarditis as in claim 1 wherein the data from the electrocardiographic monitoring is magnetically stored.

4. A method for diagnosing subacute myocarditis as in claim 1 wherein the number of cycles when the T-wave is not positive during a given time period is utilized as the numerator of a ratio whose denominator is the total number of cycles during said given time period.

5. A method for diagnosing subacute myocarditis as in claim 1, 2, 3, or 4 wherein the frequency when the T-wave is not positive is determined for a time period when the patient's pulse rate is below 100 cycles per minute such as during normal activity.

6. A method for diagnosing subacute myocarditis as in claim 1, 2, 3, or 4 wherein the frequency when the T-wave is not positive is determined for a time period when the patient's pulse rate is between 100 and 120 cycles per minute such as during moderate tachycardia.

7. A method for diagnosing subacute myocarditis as in claim 1, 2, 3, or 4 wherein the frequency when the T-wave is not positive is determined for a time period when the patient's pulse rate is above 120 cycles per minute such as during severe tachycardia.

8. A method for diagnosing subacute myocarditis as in claim 1, 2, 3, or 4 wherein the frequency when the T-wave is not positive is determined for a given time period regardless of the patient's pulse rate.

9. A method for diagnosing subacute myocarditis in a patient whose sedentary electrocardiogram ST segment and T-wave do not indicate myocarditis, the method comprising:
   utilizing a portable monitor to electrocardiographically monitor T-waves of an ambulatory patient who has unexplainable fatigue;
   magnetically storing the electrocardiographic data of the patient;
   determining the T-wave frequency when the T-wave of the patient is not positive; and
   providing a diagnosis of subacute myocarditis based on the determination of T-wave frequency.

10. A method for diagnosing and treating subacute myocarditis in a patient whose sedentary electrocardiogram ST segment and T-wave do not indicate myocarditis, the method comprising:
    electrocardiographically monitoring to detect T-waves of an ambulatory patient who has unexplainable fatigue;
    determining the T-wave frequency when the T-wave of the ambulatory patient is not positive;
    providing a diagnosis of subacute myocarditis when there is an excessively high frequency of the T-wave not being positive; and
    prescribing a treatment when subacute myocarditis is diagnosed.

11. A method for diagnosing and treating subacute myocarditis as in claim 10 wherein the treatment prescribed is selected from the group consisting of restricting activity and refraining from the intake of alcohol, antiviral chemotherapy and immunomodulators.

12. A method for diagnosing and treating subacute myocarditis as in claim 10 or 11 wherein recovery is monitored by performing further electrocardiographic monitoring of the treated ambulatory patient and determining the frequency when the T-wave is not positive.

13. A method for diagnosing and treating subacute myocarditis in a patient whose sedentary electrocardiogram ST segment and T-wave do not indicate myocarditis, the method comprising:
    utilizing a portable monitor to electrocardiographically monitor T-waves of an ambulatory patient who has unexplainable fatigue;
    magnetically storing the electrocardiographic data of the patient;
    determining the T-wave frequency when the T-wave of the ambulatory patient is not positive;
    providing a diagnosis of subacute myocarditis when there is an excessively high frequency of the T-wave not being positive; and
    prescribing a treatment that includes both restricting activity and refraining from the intake of alcohol when subacute myocarditis is diagnosed.

14. A method for diagnosing and treating subacute myocarditis as in claim 13 wherein additional treatment prescribed is selected from the group consisting of antiviral chemotherapy and immunomodulators.

15. A method for diagnosing and treating subacute myocarditis as in claim 13 or 14 wherein further electrocardiographic monitoring of the treated ambulatory patient is performed with the portable monitor to determine the frequency when the T-wave is not positive in order to determine when the patient has recovered.

16. A method for diagnosing subacute myocarditis in a patient whose sedentary electrocardiogram ST segment and T-wave do not indicate myocarditis, the method comprising:
    electrocardiographically monitoring to detect T-waves of an ambulatory patient who has unexplainable fatigue;
    determining the extent to which the T-waves of the ambulatory patient are negative; and
    providing a diagnosis of subacute myocarditis based on the determination of the negative extent of the T-waves.

17. A method for diagnosing subacute myocarditis as in claim 16 wherein the extent to which the T-waves are negative is determined by totaling the integral sum of the negative area of the T-waves divided by the total heart beats for a given time.

18. A method for diagnosing subacute myocarditis as in claim 16 wherein the negative amplitude of the T-waves is measured to determine the extent to which the T-waves are negative.

19. A method for diagnosing subacute cardiac dysfunction in a patient whose sedentary electrocardiogram ST segment and T-wave do not indicate cardiac dysfunction, the method comprising:
    electrocardiographically monitoring to detect T-waves of an ambulatory patient who has unexplainable fatigue;
    determining the T-wave frequency when the T-wave of the ambulatory patient is not positive; and
    providing a diagnosis of subacute cardiac dysfunction based on the determination of T-wave frequency.

20. A method for diagnosing subacute cardiac dysfunction in a patient whose sedentary electrocardiogram ST segment and T-wave do not indicate cardiac dysfunction, the method comprising:
    electrocardiographically monitoring to detect T-waves of an ambulatory patient who has unexplainable fatigue;
    determining the extent to which the T-waves of the ambulatory patient are negative; and
    providing a diagnosis of subacute cardiac dysfunction based on the determination of the negative extent of the T-waves.

* * * * *